United States Patent [19]

Weber et al.

[11] 4,288,410
[45] Sep. 8, 1981

[54] APPARATUS FOR PREPARING ALUMINUM ALKOXIDES

[75] Inventors: Willis W. Weber, South Salem; Richard F. Hill, Cold Spring, both of N.Y.; Thomas J. Weeks, Jr., Columbus, Ohio

[73] Assignee: Union Carbide Corporation, New York, N.Y.

[21] Appl. No.: 169,757

[22] Filed: Jul. 17, 1980

Related U.S. Application Data

[62] Division of Ser. No. 32,640, Apr. 23, 1979, Pat. No. 4,242,271.

[51] Int. Cl.³ .............................................. B01J 8/02
[52] U.S. Cl. .................................... 422/233; 210/205; 260/448 AD; 422/189
[58] Field of Search ...................... 422/189, 232, 233; 260/448 AD; 210/205; 423/630; 252/463

[56] References Cited

U.S. PATENT DOCUMENTS

| | | | |
|---|---|---|---|
| 2,615,906 | 10/1952 | Stanton | 422/189 X |
| 2,636,865 | 4/1953 | Kimberlin, Jr. | 260/448 AD |
| 2,666,076 | 1/1954 | Rex et al. | 422/189 X |
| 2,730,239 | 1/1956 | Peery | 210/205 |
| 2,749,216 | 6/1956 | Dinwiddie et al. | 423/630 |
| 2,762,783 | 9/1956 | Kimberlin, Jr. et al. | 252/463 |
| 2,845,447 | 7/1958 | Carlson et al. | 260/448 AD |
| 2,965,663 | 12/1960 | Smith et al. | 260/448 AD |
| 3,060,005 | 10/1962 | Litchfield | 422/233 X |
| 3,078,225 | 2/1963 | Maier et al. | 210/205 X |
| 3,094,546 | 6/1963 | Towers | 260/448 AD |
| 3,121,680 | 2/1964 | Ciabattari | 210/205 X |
| 3,446,828 | 5/1969 | Buzas et al. | 260/448 AD |
| 3,970,562 | 7/1976 | Motozawa et al. | 210/205 |
| 3,992,300 | 11/1976 | Hill | 210/205 X |
| 4,059,524 | 11/1977 | Chataigner et al. | 210/205 X |

Primary Examiner—Richard L. Chiesa
Attorney, Agent, or Firm—Harrie M. Humphreys

[57] ABSTRACT

Aluminum alkoxides are prepared by the reaction of impure aluminum and monohydric alcohols in a process wherein impure metallic aluminum particles are continuously fed at a metered rate into a stoichiometric excess of alcohol. The novel apparatus disclosed permits the continuous introduction of the aluminum particles into the reactor and removal of non-reactive impurities through columns of ambient temperature alcohol which avoids contact of atmospheric oxygen with the reaction products.

1 Claim, 2 Drawing Figures

APPARATUS FOR PREPARING ALUMINUM ALKOXIDES

This application is a division of our prior U.S. application Ser. No. 032,640, filed Apr. 23, 1979, and now U.S. Pat. No. 4,242,271.

The present invention relates in general to the preparation of aluminum alkoxides and to a novel apparatus for carrying out the process. More particularly, it relates to the preparation of aluminum alkoxides from aluminum metal and an alcohol and to an improved apparatus for accomplishing the required reaction on a continuous basis.

Aluminum alkoxides are employed as catalysts and as intermediates in a variety of pharmaceutical and industrial processes. Aluminum isopropoxide is well known and widely used as a selective reducing agent for aldehydes and ketones. One of the largest current industrial uses is as an intermediate in the preparation of aluminas, which are obtained directly by hydrolysis of the alcoholate. Although several processes for obtaining the aluminum alkoxides have been proposed, the most commonly employed at present in the reaction between metallic aluminum and a monohydric alcohol.

For a number of reasons, even this generally preferred process is difficult, if not hazardous, to carry out, particularly on a commercial scale, and commonly results in an aluminum alkoxide product which is too impure for use directly in a number of applications.

From the operational standpoint, a principal source of potential hazard is the highly exothermic nature of the reaction—approximately 9.5 kcal./mole of aluminum. Although catalysts such as iodine or mercuric chloride are sometimes employed to initiate the reaction, the heat generated is more than adequate to sustain the reaction and means must be used to control the liberation of excessive amounts of energy to avoid an explosive situation. Also, the by-product of the reaction of the aluminum and the alcohol is hydrogen. In order to avoid the generation of undue pressures in the reactor, not only is it necessary to control the reaction rate; but in all events it is also necessary to provide a means of removing the hydrogen from the reactor without undue loss of alcohol reactant.

It is also essential to avoid introduction of air into the reactor to prevent the formation of a potentially explosive mixture with the evolved hydrogen and/or the alcohol vapors.

Because of the foregoing problems, it has formerly been the practice to limit the proportion of alcohol reactant permitted to contact the mass of aluminum at any given time either by diluting the alcohol with an unreactive hydrocarbon, or by metering the flow rate of alcohol into the reactor where it contacts the aluminum. In the first case, it is necessary to isolate the alkoxide product from the hydrocarbon prior to its ultimate use, and in the second case, the duration of the process is limited by the charge of aluminum initially present since it is difficult to introduce additional aluminum without interrupting the operation of the process unless expensive standby apparatus is employed.

It is, therefore, the principal objective of the present invention to provide an improved process for producing aluminum alkoxides which can be operated in a truly continuous manner and in which commercial scale operation is readily accomplished safely and economically. It is a further objective to provide a novel apparatus for carrying out the process.

In accordance with the present invention the novel process comprises (a) providing a reactor containing in the liquid phase a monohydric alcohol containing from 1 to 10 carbon atoms, at a temperature of from 15° C. to 231° C.;

(b) introducing impure metallic aluminum from an air environment into the lower portion of said reactor and below the surface level of the alcohol therein by passing said impure aluminum downwardly through a feed column of said alcohol in the liquid phase at a temperature of not greater than 40° C. whereby any entrained air entering said feed column is returned to the atmosphere in the form of bubbles, said downward passage of the aluminum through said alcohol being sufficiently rapid that reaction between the aluminum and the alcohol is not initiated;

(c) conveying the impure aluminum upward through the alcohol in the reactor while reacting the aluminum value thereof with the said alcohol thereby forming hydrogen as a reaction by-product, colloidal particles of the impurity constituent of the impure aluminum, and a residue of sludge comprising the bulk of the said impurity constituent;

(d) conveying the sludge residue out of said reactor upwardly through a conduit containing alcohol at a temperature of not more than 40° C. at its egress end, said conduit communicating with the reactor through an orifice connection located below the surface of the liquid in the reactor; and (e) introducing impure aluminum into a stoichiometric excess of alcohol in said reactor and removing hydrogen and product aluminum alkoxide from said reactor at rates which provide self-regulation of the rate of production of the aluminum alkoxide product.

Optionally, following step (d) supra, the sludge residue may be passed through a heated conveyor to vaporize contained alcohol. The alcohol vapors are returned to the reactor for recovery in a condenser system, thus reducing the alcohol consumption and producing a more easily disposable dry sludge.

Strictly speaking, any and all commercially feasible metallic aluminum, regardless of the method of its manufacture and purification, will be to some degree impure, i.e., contains at least measurable amounts of heavy metals. In general, however, commercial aluminum stock contains far more than trace quantities of other elements and/or compounds. These impurities can be either intentionally added, as in the case of aluminum alloys, or be present as an incidental result of its production, fabrication, use, transport, storage and the like. The present process is extremely tolerant of aluminum impurities and can employ with equally satisfactory results such diverse aluminum raw materials as primary ingot, foil, salvaged beverage containers, shot, mill and factory scrap such as turnings, punchings, shavings and wire, and even dross. Dross, which has a slag-like appearance, is formed when molten aluminum is poured from the Hall electrolytic cell into a casting furnace. During this procedure, some of the metal is oxidized and entrains additional metal. A typical composition of dross is as follows:

| Element | Conc., Wt.-% | Element | Conc., Wt.-% |
|---|---|---|---|
| Mn | 0.03–0.2 | Si | 0.1–0.4 |
| Ni | 0.01–0.07 | Cr | 0.02–0.07 |

-continued

| Element | Conc., Wt.-% | Element | Conc., Wt.-% |
|---------|--------------|---------|--------------|
| Cu | 0.005-0.02 | V | 0.4-1 |
| Ti | 0.04-0.2 | Mg | 0.1-0.6 |
| Fe | 0.06-0.3 | Zn | 0.008-0.03 |
| Be | 0.0004 | Sn | 0.008-0.02 |
| Ca | 0.2-0.6 | B | 0.08-0.4 |
| Co | 0.02-0.08 | W | 0.06-0.25 |
| Al | 29 | $Al_2O_3$ | 55.1 |
| C | 0.14 | $Na_3AlF_6$ | 12.9 |

Accordingly, the term "impure aluminum" as used in this specification and in the claims is intended to mean any aluminum which contains at least 0.01 weight percent of elements other than aluminum. As a practical matter, this includes all commercially available aluminum.

It has been found that dross is remarkably reactive in the present process and is a preferred source of aluminum metal. Typically, 80% of its aluminum metal content is converted to aluminum alkoxide. It is sometimes desirable to beneficiate the raw dross material by first crushing the mass and then removing the fines by screening. The friable alumina in the dross fractures upon impact during the crushing operation, while the ductile aluminum remains as coarser particles. Selection of appropriate particle size for dross tends to reduce the amount of unreactive solids subsequently discharged from the reactor. It has been found that a particle size range corresponding to a mesh size range of 3 to 7 (U.S. Standard Sieve Series), but preferably between about 3-mesh and 5-mesh (i.e. particles of about 4-7 mm. in largest dimension) gives quite satisfactory results from the standpoint of reaction rate and yield of alkoxide. Dross particles can advantageously be water-washed before use. Mill and factory scrap with oily coatings is preferably degreased before being fed to the reactor.

The alcohol reactant is one or a mixture of two or more monohydric, preferably primary or secondary, alcohols containing from 1 to 10, preferably 2 to 6, carbon atoms. The pentanols are further preferred because of their immiscibility with water, with n-pentanol (b.p. 138° C.) being particularly preferred for use in the present process. The alcohol reagent should be as dry (water-free) as is reasonably possible since water readily converts the alkoxide product to alumina, $Al_2O_3$, which is removed from the reactor as a part of the sludge impurity.

By virtue of the novel apparatus of this invention, it is possible to control the rate of the reaction by controlling the rate of introducing the aluminum metal.

During the course of the reaction, aluminum is delivered to the lower portion of the reactor by descending through a conduit containing alcohol sufficiently cool to prevent reaction initiation. The ingress end of this conduit is safely exposed to the atmosphere and accordingly, air entering the conduit along with the aluminum-containing feed readily returns to the atmosphere while the aluminum descends downwardly through the conduit, and ultimately enters the reaction zone of the reactor free of entrained air. This ability to inject additional aluminum to the reaction zone at any time and in any quantity has the additional advantage of maintaining optimum reaction rates even though the aluminum values of the impure feedstock fluctuate widely. This is especially beneficial when feedstock as impure as dross is employed.

Although other means are available, it has been found that the evolution of hydrogen gas as a by-product serves extremely well as an indicator of the reaction rate. The evolved hydrogen is conveniently removed from the reactor through a reflux vent which is cooled to condense out alcohol vapors and return them to the reactor. The hydrogen steam is passed through a metering device which, through means well known in the art, can be interconnected with the device which feeds aluminum into the reactor.

The alcohol reagent can also be continually or intermittently introduced into the reaction zone. Being liquid, there is no difficulty in avoiding the introduction of entrained air as in the case of aluminum, and any standpipe which enters the reactor below the liquid level in the reactor or a U-tube device, or the like will suffice. A preferred method of introducing a portion of alcohol reagent is through the alcohol-containing conduit through which the sludge impurities are conveyed upwardly through the reaction zone and out of the reactor. The addition of alcohol reagent countercurrently through this conduit results in washing alkoxide products from the sludge particles and increases the product yield. The remaining portion of the alcohol feed is advantageously added through the aluminum feed conduit where it acts to prevent alkoxide product from diffusing upwardly therein.

The alkoxide product can continuously or intermittently be removed from the reactor through a tap, preferably located in the reactor wall at a position which permits the removal of principally alkoxide with a minimum quantity of alcohol. The product alkoxide can be recovered and purified in the known manner.

Figure 1:
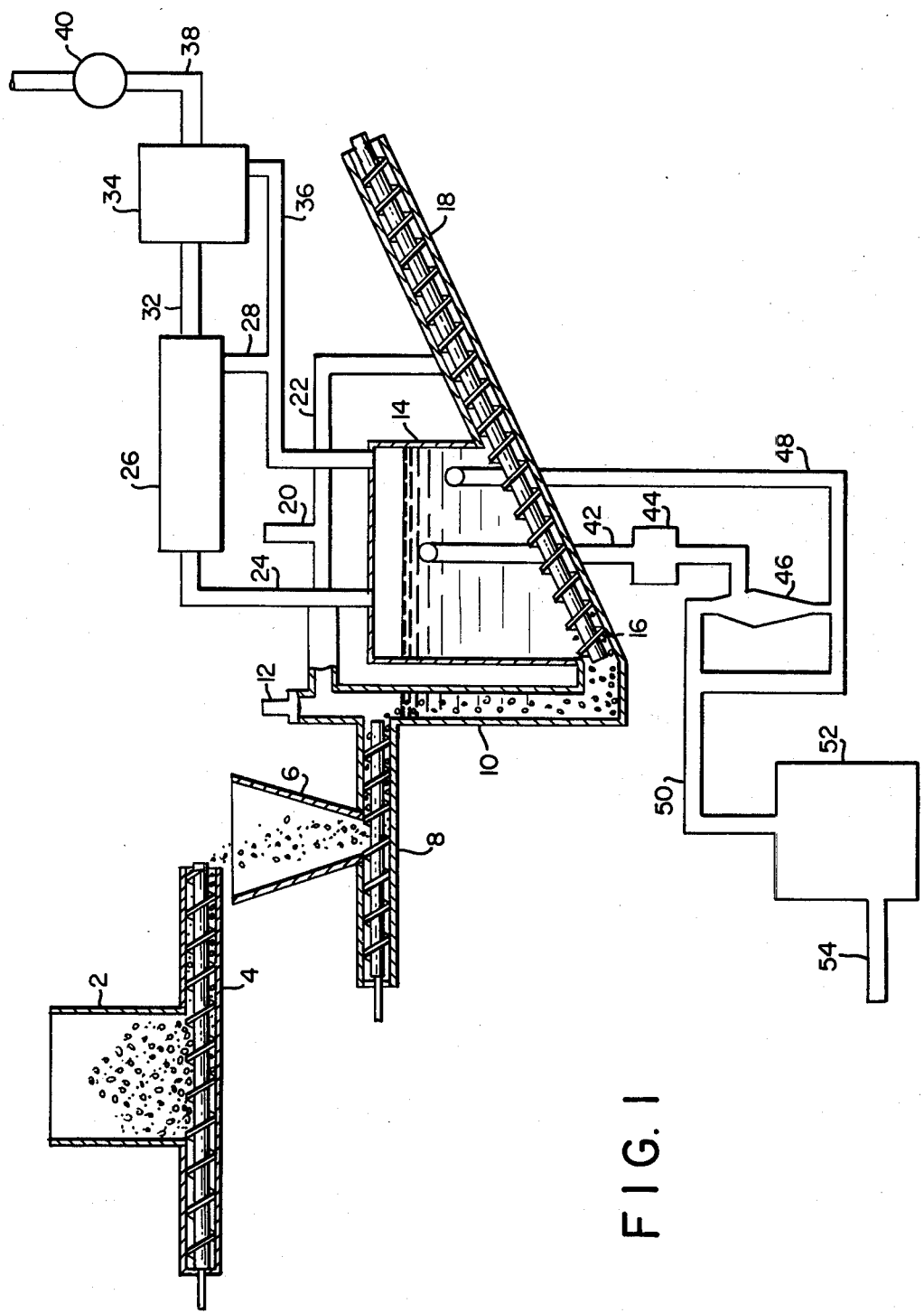
FIG. 1 is a schematic flow diagram of the reaction process.

With reference of FIG. 1, the present process typically operates in the following manner: Particulate metallic aluminum such as dross is conveyed from feed storage container 2 by screw conveyor 4 into hopper 6 and thence at a predetermined feed rate through conveyor screw 8 into vertical conduit 10 of the reactor which contains n-pentanol below the point of introduction of the aluminum particles. During the descent of the aluminum particles through the n-pentanol in conduit 10, any entrained air bubbles rise therethrough and can be removed through vent 12 which is open to the atmosphere. At the bottom of conduit 10, the aluminum particles are slowly conveyed via screw conveyor 16 upwardly through the reaction zone 14 in contact with the n-pentanol and aluminum n-pentyloxide reaction product therein contained. During the passage through reaction zone 14 the aluminum is permitted to react with the n-pentanol to form the alkoxide product and the residual impurity elements of the aluminum feed are continued to be conveyed out of the reaction zone through conduit 18 for disposal. n-Pentanol is continually fed into the reaction zone 14 through conduits 20 and 22 which distributes the alcohol feed into conduit 10 and conduit 18. The flow in conduit 10 cocurrent with the aluminum particles tends to retain the alkoxide reaction product in the reaction zone, and the flow through conduit 18 countercurrent to the movement of the solid unreacted impurities or sludge results in a washing action which removes alkoxide product from the sludge particles surface and returns the product to the reactor. Hydrogen gas, which is a reaction by-product, and volatilized n-pentanol from the reaction zone 14 are passed through conduit 24 to a primary condenser 26 wherein the bulk of the n-pentanol is condensed and returned to the reaction zone through conduits 28 and 30. The hydrogen and residual alcohol vapor is passed from primary condenser 26 through conduit 32 to secondary condenser 34 where essentially all of the alcohol of the gas stream is condensed and returned to the reaction zone through conduits 36 and 30. The hydrogen is removed from the system through conduit 38 and metering device 40. The volume of hydrogen produced can conveniently serve as a monitoring means to determine the rate of the alkoxide-producing reaction, and can readily be correlated with the aluminum feeding device to render the system self-controlling. Alkoxide product, alcohol and suspended fine unreacted aluminum particles are withdrawn through conduit 42 and are passed by means of pump 44 to cyclone separator 46. The solids are discharged from the separator into conduit and the liquid through conduit 50. A portion of the liquid stream is diverted through conduit 48 and is returned along with the solids to the reactor. The other liquid comprising the alkoxide product and alcohol are passed to surge tank 52 and thence out of the system for further processing and separation through conduit 54.

In general, the improved apparatus of the present invention comprises (a) an enclosed reactor adapted to contain a reactive mass of alcohol in the liquid state; (b) a vertically disposed feed column, communicating with said reactor through an inlet orifice located in the lower portion of said reactor, said feed column having an ingress opening to the atmosphere higher than the inlet orifice in said reactor whereby a portion of said feed column is filled with alcohol when said reactor is charged with alcohol to a point above the inlet orifice; (c) means for depositing impure aluminum particles into the ingress opening of said feed column; (d) a sludge removal column providing a conduit connecting the interior of the said reactor at a point below the surface of the liquid mass to be contained therein and the external atmosphere at a point having the same elevation as the surface of the said liquid mass in said reactor; (e) means for transporting deposited impure aluminum particles from the inlet orifice of said reactor upwardly through said reactor in intimate contact with the liquid alcohol mass to be contained therein, and for conveying unreacted impurities associated with said aluminum particles out of said reactor through the said sludge removal column; and (f) means for venting gases and vapors from the upper portion of the reactor.

Figure 2:
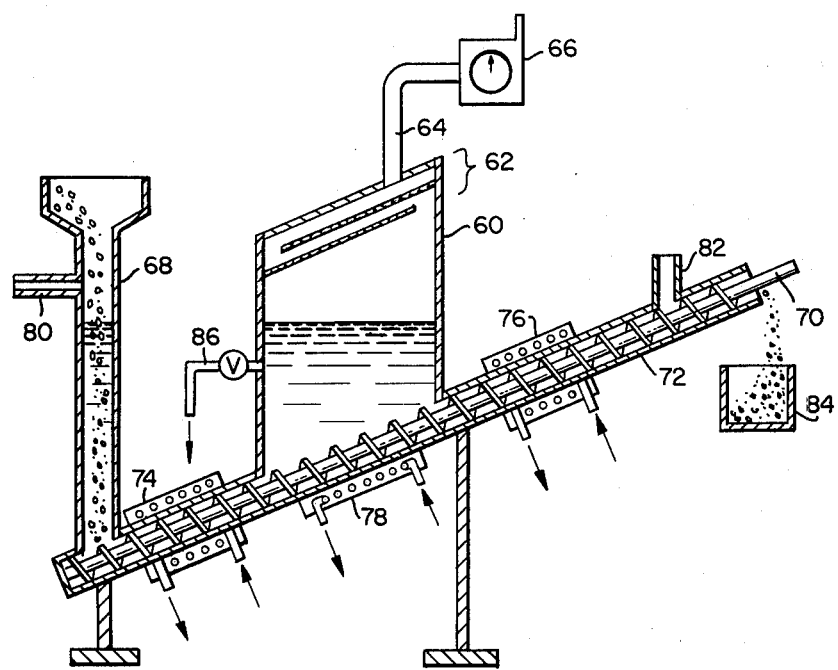
FIG. 2 is a cross-sectional side view of one embodiment of the reactor apparatus of this invention.
Figure 1:
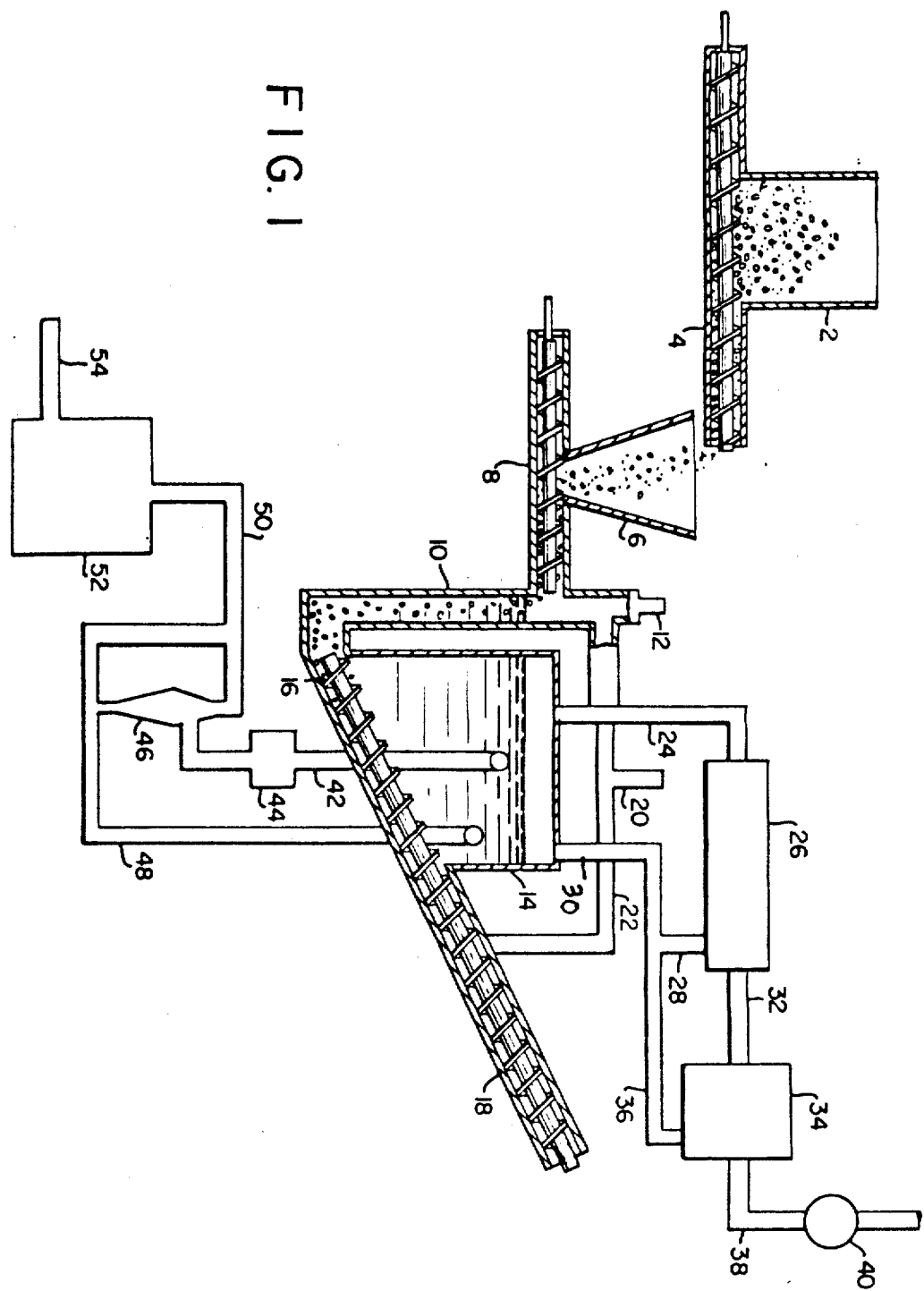

A specific embodiment of the apparatus of this invention is shown in FIG. 2 of the drawings. With reference thereto, reactor 60 is a container of any desired configuration which serves to contain the alcohol reagent at a temperature of from about ambient to 231° C. A condenser 62 is located in the upper portion of the reactor in the vapor space over the alcohol and serves to condense alcohol and/or alkoxide vapors and return them to the reaction zone. Vent conduit 64 is provided to conduct the non-condensible $H_2$ gas generated as a reaction by-product out of the reactor and through meter 66. Introduction of the metallic aluminum particles into the reactor is accomplished by means of feed column 68 which is at least partially filled with the alcohol reagent and serves to remove entrained and absorbed oxygen which may enter along with the aluminum particles. The particles are conveyed into the reactor 60 from the bottom of feed column 68 by screw conveyor 70 which enters the reactor near the bottom and is angled upward through the alcohol mass in the reactor and emerges inside the sludge removal column 72. Cooling jackets 74 and 76 are positioned adjacent to the reactor surrounding the screw conveyor 77 to chill the alcohol in order to prevent pre-initiation of the reaction before the aluminum enters the reactor and the continued reaction of any reactive aluminum leaving the reactor along with the inactive impurity content of the aluminum feed. The sludge removal column 72 extends upwardly from the reactor 60 and terminates with an opening to the atmosphere that is above the level of the liquid in the reactor. Heat to raise the alcohol reagent to the reaction initiation temperature initially is provided by heating jacket 78. Both feed column 68 and sludge removal column 72 are provided with inlet tubes, 80 and 82, respectively to permit the introduction of alcohol reagent to the reactor during the course of the reaction. A sludge pot 84 is provided to contain sludge forced out through sludge removal column 72. The alkoxide product is withdrawn from the reactor through tap 86.

What is claimed is:

1. Apparatus suitable for use in the preparation of aluminum alkoxide by the reaction of a monohydric alcohol and impure aluminum which comprises
   (a) an enclosed reactor adapted to contain a reactive mass of alcohol in the liquid state;
   (b) a vertically disposed feed column communicating with said reactor through an inlet orifice located in the lower portion of said reactor, said feed column having an ingress opening to the atmosphere higher than the inlet orifice in said reactor whereby a portion of said feed column is filled with alcohol when said reactor is charged with alcohol to a point above the inlet orifice;
   (c) means for depositing impure aluminum particles into the ingress opening of said feed column;
   (d) a sludge removal column providing a conduit connecting the interior of the said reactor at a point below the surface of the liquid mass to be contained therein and the external atmosphere at a point having the same elevation as the surface of the said liquid mass in said reactor;
   (e) means for transporting deposited impure aluminum particles from the inlet orifice of said reactor upwardly through said reactor in intimate contact with the liquid alcohol mass to be contained therein, and for conveying unreacted impurities associated with said aluminum particles out of said reactor through the said sludge removal column; and
   (f) means for venting gases and vapors from the upper portion of the reactor.

* * * * *

UNITED STATES PATENT AND TRADEMARK OFFICE
CERTIFICATE OF CORRECTION

PATENT NO. : 4,288,410

DATED : September 8, 1981

INVENTOR(S) : Weber, et al.

It is certified that error appears in the above—identified patent and that said Letters Patent is hereby corrected as shown below:

Delete Figure 1 of the drawings and substitute the attached sheet therefore.

Signed and Sealed this

Twelfth Day of January 1982

[SEAL]

Attest:

GERALD J. MOSSINGHOFF

Attesting Officer     Commissioner of Patents and Trademarks